United States Patent [19]

Schouteeten

[11] Patent Number: 5,489,705
[45] Date of Patent: Feb. 6, 1996

[54] SODIUM SALT OF 1-MENTHYLOXYCARBONYL 1-HYDROXY METHANESULPHONIC ACID, ITS PREPARATION PROCESS AND ITS USE FOR OBTAINING L(-)MENTHYL GLYOXYLATE

[75] Inventor: Alain Schouteeten, Ezanville, France

[73] Assignee: Societe Francaise Hoechst, Puteaux, France

[21] Appl. No.: 416,329

[22] Filed: Apr. 4, 1995

Related U.S. Application Data

[62] Division of Ser. No. 317,381, Oct. 4, 1994, Pat. No. 5,442,090.

[30] Foreign Application Priority Data

Oct. 5, 1993 [FR] France .................. 93 11842

[51] Int. Cl.$^6$ .................. C07C 303/00
[52] U.S. Cl. .................. 560/149
[58] Field of Search .................. 562/149

[56] References Cited

PUBLICATIONS

Chemical Abstracts 74:140858, 1970 Jurczak.
Sythetic Communications, vol. 20, No. 18, 1990 New York, US, pp. 2837–2847. F. Fernandez, et al.: "A useful synthesis of Chiral Glyoxylats".

Journal Of Organic Chemistry, vol. 35, No. 11, Nov. 1970, Washinton, D.C., US, pp. 3691–3694, L. Hub et al.: "Alpha–Methoxy–alphatrifluoromethylphenylacetic acid. Configuration by asymmetric synthesis."Roczniki Chemii, vol. 44, No. 11, 1970 Varsoivie, PL, pp. 2257–2259. J. Janusz, et al. "Synthesis of optically active glyoxylic acid esters."

Primary Examiner—José G. Dees
Assistant Examiner—Samuel Barts
Attorney, Agent, or Firm—Browdy and Neimark

[57] ABSTRACT

Sodium salt of 1-menthyloxycarbonyl 1-hydroxy methanesulphonic acid, its preparation process and its use for obtaining L(–)menthyl glyoxylate.
TEXT OF THE ABSTRACT Product of formula (I).

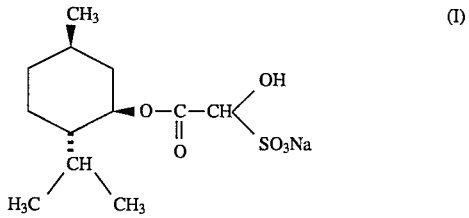

preparation process and use of the product of formula (I) according to claim 1 for obtaining the product of formula (II)

7 Claims, No Drawings

SODIUM SALT OF 1-MENTHYLOXYCARBONYL 1-HYDROXY METHANESULPHONIC ACID, ITS PREPARATION PROCESS AND ITS USE FOR OBTAINING L(-)MENTHYL GLYOXYLATE

This is a division of copending parent application Ser. No. 08/317,381 filed Oct. 4, 1994 now U.S. Pat. No. 5,442,090.

The present invention relates to the sodium salt of 1-menthyloxycarbonyl 1-hydroxy methanesulphonic acid, in its various stereoisomeric forms, its preparation process and its use for obtaining L(−)menthyl glyoxylate.

Menthol belongs to the family of 2-isopropyl 5-methyl cyclohexanol isomers which possess 3 asymmetrical carbons and therefore 8 isomers forming 4 racemics one of which is DL-menthol which is the 1α, 2β, 5α isomer. The present invention therefore relates to the sodium salt of 1-menthyloxycarbonyl 1-hydroxy methanesulphonic acid, of formula (I), which includes the sodium salt of DL-1-menthyloxycarbonyl 1-hydroxy methanesulphonic acid, the sodium salt of L(−)-1-menthyloxycarbonyl 1-hydroxy methanesulphonic acid and the sodium salt of D(+)-1-menthyloxycarbonyl 1-hydroxy methanesulphonic acid.

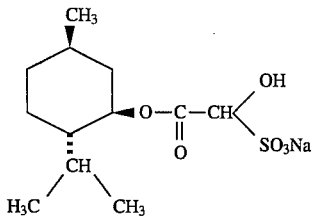

The sodium salt of 1-menthyloxycarbonyl 1-hydroxy methanesulphonic acid is the bisulphite compound of menthyl glyoxylate of formula II,

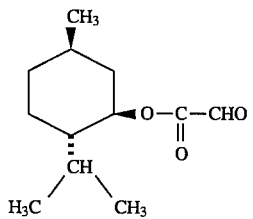

which includes D,L-menthyl glyoxylate, L(−)-menthyl glyoxylate and D(+)-menthyl glyoxylate.

L(−)-menthyl glyoxylate, designated hereafter MG, is a known product, prepared in particular either by oxidation of L(−)menthyl tartrate (F. Fernandez et al, Synthetic Comm. 1990, 2837–47), or by reduction of (−)menthyloxalyl chloride (L. Hub et al, J. Org. Chem., 35, 3691–4, 1970), or from (−)menthyl bromo acetate by means of its nitrated derivative: (−)menthyl 2-nitrooxy acetate (J. Jurczak et al, Roczniki Chem, 44, 1970, 2257). Furthermore, J. K. Whitesell et al, J. Org. Chem., 51, 4779 (1986), propose various ways to access chiral alcohol glyoxylates, one of which in particular is the direct esterification of monohydrated glyoxylic acid which allowed them to obtain, after laborious purifications, and with a poor yield, (±)–(4β, 8aα)decahydro 8α-phenyl 1-naphthalene glyoxylate.

MG is a chiral reagent which is extremely useful in asymmetrical synthesis; therefore it is desirable to obtain it easily with a high degree of purity. Obtaining it by known methods requires either expensive raw materials and/or reagents, or laborious purifications. Now the Applicant was surprised to discover that the bisulphite compound of MG, of formula (I), was obtained very easily with an almost quantitative yield, that it could, if desired, be isolated in the pure crystallized state and that in an aqueous medium, after reaction with formaldehyde, it led quantitatively, in the pure crystallized state, to L(−)menthyl glyoxylate, without it being necessary to resort to purifications by distillation, which are very expensive on an industrial scale.

Therefore a subject of the invention is the sodium salt of 1-menthyloxycarbonyl 1-hydroxy methanesulphonic acid, of formula (I), in its various possible stereoisomeric forms, which is presented in the form of colourless crystals, soluble in water, having a melting point higher than 200° C.

Among the products of formula (I), there can be mentioned:
- the sodium salt of DL-1-menthyloxycarbonyl 1-hydroxy methanesulphonic acid,
- the sodium salt of L(−)-1-menthyloxycarbonyl 1-hydroxy methanesulphonic acid.

Also a subject of the invention is a preparation process for the product of formula (I) and in particular for the sodium salt of DL-1-menthyloxycarbonyl 1-hydroxy methanesulphonic acid and for the sodium salt of L(−)-1-menthyloxycarbonyl 1-hydroxy methanesulphonic acid. This process is characterized by the fact that an aqueous solution of glyoxylic acid is reacted, at a temperature higher than or equal to 50° C., in an acid medium, with an excess of the corresponding menthol (DL or L(−) according to the sought product) with elimination by azeotropic distillation of the water present and formed with a $C_6$–$C_{10}$ hydrocarbon, then that the reaction mixture, cooled down and diluted with water, is decanted, that the organic phase is then treated at a pH of about 5 with an excess of a sulphurous acid derivative chosen from the group constituted by sodium metabisulphite and sodium hydrogensulphite in order to obtain the corresponding product of formula (I), which, if desired, is isolated by means known per se such as filtration.

The expression "$C_6$–$C_{10}$ hydrocarbon" can designate, for example, a saturated aliphatic hydrocarbon such as hexane, heptane, a saturated cyclic hydrocarbon such as cyclohexane, methylcyclohexane, an aromatic hydrocarbon such as toluene.

Under the preferred conditions for implementing the invention, the process described above is carried out in the following way:
- the condensation of glyoxylic acid with menthol is carried out starting with an aqueous solution of commercial glyoxylic acid at 50% by weight, with an excess of menthol, at the boiling temperature of the reaction medium and in the presence of a saturated linear aliphatic $C_6$–$C_7$ hydrocarbon and of catalytic quantities of a strong mineral acid such as sulphuric acid. The saturated linear aliphatic hydrocarbon is advantageously heptane. The condensation is carried out at the boiling point of the reaction medium with concomitant elimination of the water present and formed by azeotropic distillation and recycling of the azeotropic organic solvent, which allows this condensation to be easily monitored;
- when the condensation of the glyoxylic acid with the menthol is practically completed, the reaction medium, cooled down to ambient temperature, is diluted with water then it is decanted. The organic phase is collected, then it is treated, at ambient temperature, under agitation, under an inert atmosphere, for 2 to 24 hours, at a pH of 5, with an excess, either of sodium metabisulphite, or of sodium hydrogensulphite, in an approximately molar aqueous solution. In this way the bisulphite compound of the product of formula (I) crystallizes spontaneously from the reaction medium.

Since the product of formula (I) can be obtained very easily by the process described previously in the pure crystallized state, it therefore has useful properties for accessing the product of formula (II).

Also a subject of the invention is the use of the product of formula (I) for obtaining the product of formula (II) and more particularly the use of sodium L(−)-1-menthyloxycarbonyl 1-hydroxy methanesulphonate for accessing L(−)menthyl glyoxylate.

According to the invention, an aqueous solution of the product of formula (I) is treated under agitation, at ambient temperature, at a pH comprised between 7 and 8, with a slight excess of an aqueous solution of formaldehyde at 50% by weight in order to obtain, in the pure crystallized state, the product of formula (II). According to a variant of the invention, the aqueous phase of the reaction medium containing the product of formula (I) can be used to access the product of formula (II).

The following examples illustrate the invention without however limiting it.

EXAMPLE 1

A mixture constituted by:
- 37 g of a commercial aqueous solution of glyoxylic acid at 50% by weight, that being 0.25 mole of glyoxylic acid,
- 117.2 g (0.75 mole) of D,L-menthol (from JANSSEN CHIMICA),
- 0.7 g of sulphuric acid at 96% by weight, that being 6.86 mmoles,
- 171 g of n-heptane is heated to boiling point with concomitant distillation of the water by azeotropic entrainment.

After about 20 g of water has been collected (after about 30 min), the reaction medium is cooled down to ambient temperature, then it is diluted with 25 g of water and finally it is decanted. The organic phase is then agitated, for 24 hours, at ambient temperature, under an inert atmosphere, at a pH adjusted to 5, with an aqueous solution of sodium hydroxide at 45% by weight, with an aqueous solution containing 150 g of water and 28.5 g (0.15 mole) of sodium metabisulphite. The bisulphite compound of D,L--menthyl glyoxylate sought crystallizes spontaneously after 15 minutes of agitation. It is isolated by filtration, then it is washed by impasting in 150 g of n-heptane and finally it is dried to a constant weight, under reduced pressure, at 50° C. In this way 66.4 g (0.19 mole) of sodium D,L-1-menthyloxycarbonyl 1-hydroxy methanesulphonate crystallized with 2 molecules of water is obtained, in the form of colourless crystals having a melting point higher than 200° C. The yield is 76% of the calculated theoretical amount relative to the glyoxylic acid used.

| | MICROANALYSIS | | | |
|---|---|---|---|---|
| | | C % | H % | $H_2O$ %* | Ashes** |
| $C_{12}H_{21}O_6SNA,2H_2O$ | Calculated | 40.90 | 7.15 | 10.22 | 20.15 |
| MW = 352.37 | Found | 41.4 | 7.0 | 9.5 | 20.8 |

*determined by the K. FISCHER method
**sulphuric ashes

NMR$^{13}$C Analysis ($D_2O$) - spectrum in accordance with the proposed structure.

EXAMPLE 2

Example 1 is reproduced, replacing the D,L-menthol with the same quantity of L(−)-menthol. (1R, 2S, 5R, 2-isopropyl 5-methyl cyclohexanol), $[\alpha]_D^{20}$ −50.00 (C=10, EtOH). In this way sodium L(−)-1-menthyloxycarbonyl 1-hydroxy methanesulphonate, sodium 1-(1'R, 2'S, 5'R, 2'-isopropyl 5-methyl cyclohexyloxycarbonyl) 1-hydroxy methanesulphonate, crystallized with two molecules of water, is obtained in the form of colourless crystals having a melting point higher than 200° C. and $[\alpha]_D^{22}$ −49.00 (c=4.7, water).

EXAMPLE 3

A mixture constituted by:
- 148 g of an aqueous solution of glyoxylic acid at 50% by weight, that being 1 mole of glyoxylic acid,
- 468.6 g (3 moles) of L(−)menthol,
- 2.6 g (25 mmoles) of sulphuric acid at 96% by weight,
- 680 g of heptane is heated to boiling point with concomitant distillation of the water by azeotropic entrainment.

After 78 g of water has been collected, the reaction medium is cooled down to ambient temperature, then it is diluted with 100 g of water and finally it is decanted. The organic phase is then agitated for 24 hours, at ambient temperature, under an inert atmosphere at a pH adjusted to 5 with 2N soda, with 4 litres of an aqueous solution of sodium bisulphite, freshly prepared, containing 0.25 mole per litre of sodium bisulphite. At this stage, a chromatographic analysis of a sample of the organic phase shows that there is practically no more L(−)menthyl glyoxylate. After decanting, the aqueous phase is washed with 400 g of heptane. The organic phases are united in order to be recycled in another operation. The aqueous phase is treated at ambient temperature, under agitation at a pH of 7.5±0.5, with 66 g of an aqueous solution of formaldehyde at 50% by weight. The sought product crystallizes spontaneously from the reaction medium. It is isolated by filtration, then it is washed with water and finally it is dried to a constant weight under reduced pressure at 25° C. In this way 179 g (0.778 mole) of monohydrated L(−)menthyl glyoxylate is obtained in the form of colourless crystals having a melting point of 79±1° C. (literature mentioned M.P.=79° C.), and $[\alpha]_D^{22}$= −73° (c=3.7, EtOH). The NMR spectra analyses of the proton and of the $C^{13}$ are in accordance with the proposed structure. The yield is 77.8% of the calculated theoretical amount relative to the glyoxylic acid used.

The united organic phases are concentrated to a weight of about 990 g, then they are recycled in a new operation after the addition of one mole of glyoxylic acid in aqueous solution at 50% by weight, one mole of L(−)menthol and 25 mmoles of sulphuric acid at 96% by weight. Operating as previously, about 179 g of L(−)menthyl glyoxylate is obtained.

EXAMPLE 4

35.2 g (0.1 mole) of sodium L(−)-1-menthyloxycarbonyl 1-hydroxy methanesulphonate crystallized with two molecules of water is dissolved in 400 g of water, then this solution is treated at ambient temperature, under an inert atmosphere, under agitation and at a pH adjusted to about 7.5, with 3.3 g (0.11 mole) of formaldehyde in aqueous solution at 50% by weight. After a few minutes, the L(−)menthyl glyoxylate crystallizes spontaneously from the reaction medium. It is isolated by filtration, then it is washed with water, and finally it is dried to a constant weight under reduced pressure at 25° C. In this way 23 g (0.1 mole) of pure L(−)menthyl glyoxylate, crystallized with one molecule of water, is obtained.

I claim:
1. Preparation process for the product of formula (I),

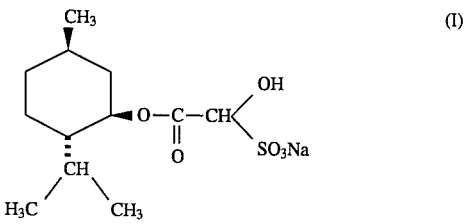

wherein an aqueous solution of glyoxylic acid is reacted, at a temperature higher than or equal to 50° C., in an acid medium, with an excess of the corresponding menthol with elimination by azeotropic distillation of the water present and formed with a $C_6$–$C_{10}$ hydrocarbon, then the reaction medium, cooled down and diluted with water, is decanted, then the organic phase is treated at a pH of about 5 with an excess of a sulphurous acid derivative of sodium metabisulphite or sodium hydrogensulphite in order to obtain a corresponding product of formula (I).

2. A process according to claim 1, wherein said menthol is L(−)menthol.

3. A process according to claim 2, wherein said aqueous solution of glyoxylic acid is an aqueous solution of glyoxylic acid at 50% by weight.

4. A process according to claim 3, wherein said $C_6$–$C_{10}$ hydrocarbon is a $C_6$–$C_7$ saturated linear aliphatic hydrocarbon.

5. A process according to claim 1, wherein said aqueous solution of glyoxylic acid is an aqueous solution of glyoxylic acid at 50% by weight.

6. A process according to claim 5, wherein said $C_6$–$C_{10}$ hydrocarbon is a $C_6$–$C_7$ saturated linear aliphatic hydrocarbon.

7. A process according to claim 1, wherein said $C_6$–$C_{10}$ hydrocarbon is a $C_6$-$C_7$ saturated linear aliphatic hydrocarbon.

* * * * *